United States Patent

Williams et al.

[11] 4,050,576
[45] Sept. 27, 1977

[54] POLYMERIC STERILANT ASSEMBLY

[75] Inventors: Joel L. Williams, Cary; Jerry J. Tulis, Raleigh; Larry A. Taylor, Hillsborough, all of N.C.

[73] Assignee: Becton, Dickinson and Company, Rutherford, N.J.

[21] Appl. No.: 715,162

[22] Filed: Aug. 17, 1976

[51] Int. Cl.² ............... B65D 81/24; A61L 3/00; A61L 13/02
[52] U.S. Cl. .................. 206/210; 21/58; 21/84; 21/85; 21/89; 21/110; 206/363
[58] Field of Search ............... 21/58, 82 R, 82 H, 84, 21/85, 88, 89, 110; 260/615.5; 206/210, 438, 363

[56] References Cited

U.S. PATENT DOCUMENTS

| | | | |
|---|---|---|---|
| 3,494,726 | 2/1970 | Barasch | 21/58 |
| 3,630,348 | 12/1971 | Benson et al. | 21/58 X |
| 3,923,154 | 12/1975 | Tullis et al. | 206/210 |
| 3,939,971 | 2/1976 | Tullis | 206/210 X |
| 3,942,634 | 3/1976 | Gandi et al. | 206/210 |

OTHER PUBLICATIONS

Walker, J. F.; Formaldehyde; Reinhold Publishing Corp.; N.Y.; 1967; pp. 140-150, 158-163, 187-191 and frontpiece.

*Primary Examiner*—Barry S. Richman
*Attorney, Agent, or Firm*—Marn & Jangarathis

[57] ABSTRACT

Sterilant package including a polyacetal, which contains oxymethylene groups and stabilizing groups therefor, such as oxyethylene groups, which has been irradiated to effect chain cleavage, without depolymerization, whereby upon subsequent heating, the polyacetal is depolymerized with increased release of formaldehyde sterilizing gas.

13 Claims, 1 Drawing Figure

U.S. Patent     Sept. 27, 1977     4,050,576
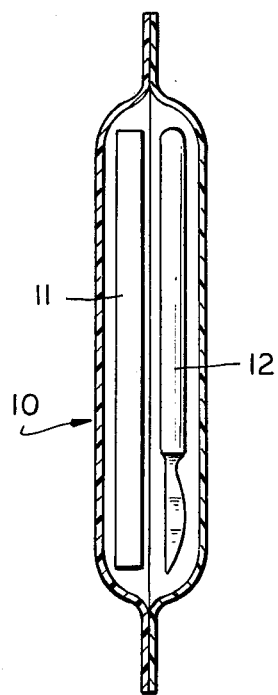

POLYMERIC STERILANT ASSEMBLY

This invention relates to sterilant packages, and more particularly, to sterilant packages which include a formaldehyde releasing substance.

Sterilant packages which include a formaldehyde releasing substance are presently known in the art. In brief, the package includes an article to be sterilized and a formaldehyde releasing substance. When the article is to be used, the package is heated to effect release of formaldehyde, with such released formaldehyde effecting sterilization of the article.

In accordance with the present invention, there is provided a sterilant package which includes a stabilized formaldehyde releasing polyacetal which has been preirradiated to effect increased formaldehyde release upon heating of the polyacetal.

More particularly, formaldehyde releasing polyacetals include recurring oxymethylene groups [—OCH$_2$—] and such polyacetals are generally stabilized by including stabilizing groups within or as endcaps for the polymer chain. The stabilizing group is generally a group including carbon-to-carbon single bonds which are free of interfering functional groups, with the preferred type of group being an —OR— group wherein R is a divalent radical including at least two carbon atoms directly linked to each other and included in the polymer chain between the two valences, with any substituents on the R radical being inert; i.e., free of interfering functional groups. As hereinabove noted, the polyacetal can include such stabilizing groups interspersed in the polymer chain or as end-caps, and in general, such polyacetals include from about 60 to 99.6, and preferably 85 to 99.6 mol percent, of oxymethylene groups, with the remainder being such stabilizing groups.

The stabilizing groups are preferably derived from cyclic ethers having adjacent carbon atoms, and as representative examples of such cyclic ethers there may be mentioned: ethylene oxide; 1,3-dioxolane; 1,3,5-trioxepane; 1,3-dioxane; trimethylene oxide; pentamethylene oxide; 1,2-propylene oxide; 1,2-butylene oxide; neopentyl formal; paraldehyde; tetrahydrofuran and butadiene monoxide. The stabilizing groups are preferably derived from dioxolane and/or ethylene oxide, with such stabilizing groups being included within the polymer chain, whereby the polymer chain includes oxymethylene groups and stabilizing oxyethylene groups.

Polyacetals which include oxymethylene groups and a stabilizing group, as end groups or caps or interspersed in the polymer chain, are well known in the art and no further details in this respect are deemed necessary for a complete understanding of the present invention. Such polyacetals are hereinafter generically referred to as stabilized polyacetals or stabilized oxymethylene containing polyacetals.

In accordance with the present invention, the stabilized polyacetal is subjected to high energy irradiation, without effecting depolymerization thereof, and as a result of such irradiation, the polyacetal can be depolymerized by slight heating with increased formaldehyde release. Although Applicant does not intend to limit the present invention by theoretical reasoning, it is believed that the high energy irradiation effects chain cleavage, without depolymerization, whereby upon subsequent heating, the polyoxymethylene chain can "unzip" to the next stabilizing group, thereby increasing formaldehyde release. Such a mechanism is shown schematically where A represents oxymethylene groups and B represents a stabilizing group, such as oxyethylene:

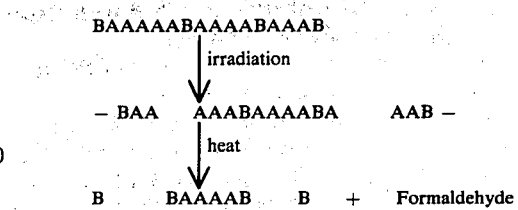

Thus, as a result of the irradiation, oxymethylene groups are cleaved from stabilizing groups, and such oxymethylene groups can be depolymerized by heating, resulting in increased formaldehyde release.

The high energy irradiation applied to the stabilized polyacetal can be in the form of gamma-, high-energy electron, UV, plasma (r.f. or microwave) or other types of irradiation known in the art. The stabilized polyacetal is subjected to a dose sufficient to effect chain cleavage, without depolymerization, with the chain cleavage, and formaldehyde release, being increased by an increase in the absorbed radiation dose. In general, the polyacetal is subjected to a dose in the order of from about 0.01 to about 400 megarads, and preferably in the order of from about 0.1 to about 40 megarads.

The formaldehyde releasing polyacetal can be employed in any one of a wide variety of forms; e.g., film, tubing, powder, etc. The formaldehyde releasing polyacetal can be included in the sterilant package either as a separate entity or as an integral part of the package. Thus, for example, a separate strip of the preirradiated polyacetal can be incorporated into the sterilant package or the package itself or a portion of the package; e.g., an inner liner, can be formed of the preirradiated polyacetal.

In accordance with one embodiment of the present invention, the polyacetal can be included in another polymer, as a dispersion or filler, thereby combining the formaldehyde releasing properties of the polyacetal with the properties of the other polymeric material.

The polyacetal dispersion or filler in this case can be from 1% to essentially 80% of the composite. The composite can exist in any geometrical form but would most often be in a fiber or film form. Mixing and formation of composites into various forms generally take place in conventional mixers, molders, and extruders which are all familiar equipment to people in the area of polymer conversion. The remaining part of the composite can be virtually any polymeric material. For example polyolefins, polyesters, and polyamides; however, the present invention is not limited to such materials.

The sterilant package includes the polyacetal in an amount sufficient to provide an amount of formaldehyde for sterilizing the contents of the package. As a result of the increased formaldehyde release, the total amount of polyacetal included in the package is reduced.

The amount of formaldehyde released can vary from about 0.1 mg/gram of polymer to 100 mg/gram of polymer. For most sterilizing applications 1.0 mg/gram to 30.0 mg/gram will suffice to sterilize the article contained in the bag.

Formaldehyde can be generated from the irradiated polyacetal included in the package by heating thereof. In general, formaldehyde can be generated by heating to temperatures in the order of from about 35° C to about 200° C. A more preferred range is from 50° C to about 90° C.

The invention will be further described with respect to the accompanying drawing wherein:

The drawing illustrates an embodiment of the sterilant package of the present invention.

Referring to the drawing, there is shown a sterilant package 10, including an article to be sterilized 12 and as a separate piece, a stabilized polyacetal film 11 which has been preirradiated in accordance with the invention to increase formaldehyde release therefrom. The package can be formed, for example, from clear polyester film sheets which are heat sealed to each other. The article 12 is sterilized by formaldehyde release from the film 11 by effecting heating of the package.

It is to be understood that the present invention is not to be limited by the hereinabove described embodiment in that the present invention, as hereinabove described, is equally applicable to other forms and types of sterilant packages.

The invention will be further described with respect to the following examples; however, the scope of the invention is not to be limited thereby.

Example 1

A polyoxymethylene (99 mol % oxymethylene and 1.0 mol % of oxyethylene) film (0.005 cm thick) was tested for formaldehyde release at 90° C for 1 hour and found to yield only 0.05 mg gas per gram of film. A duplicate sample that had been gamma irradiated to 3.0 megarads was found to release 0.75 mg/g under otherwise similar conditions. This amount of free formaldehyde in a separate set of experiments was capable of sterilizing items enclosed in a sealed bag.

Example 2

A polyoxymethylene film as described in Example 1 except irradiated to 4.5 megarads was found to release 2.54 mg/g of formaldehyde.

Example 3

A polyoxymethylene film as described in Example 1 except irradiated to 17 megarads was found to release 4.38 mg/g of formaldehyde.

Numerous modifications and variations of the present invention are possible in light of the above teachings and, therefore, within the scope of the appended claims, the invention may be practiced otherwise than as particularly described.

What is claimed is:

1. An article of manufacture, comprising: a sterilant package, said sterilant package including in the interior of such package a polyacetal containing oxymethylene groups and stabilizing groups linked to the oxymethylene groups to prevent chain cleavage, said polyacetal having been subjected to high energy irradiation, prior to subjecting said package to heat sterilization, in a dose of from 0.01 to 400 megarads sufficient to effect chain cleavage without depolymerization to increase formaldehyde release upon subsequent heating of the package.

2. The article of claim 1 wherein at least an interior portion of the package is formed from the polyacetal.

3. The article of claim 1 wherein the polyacetal is included as a separate piece in the package.

4. The article of claim 1 wherein the package is formed of a polymer film having the polyacetal dispersed therein.

5. The article of claim 1 wherein the package includes an article to be sterilized.

6. The article of claim 1 wherein the irradiation dose was from 0.1 to 40 megarads.

7. The article of claim 1 wherein the stabilizing group is —OR— wherein R is a divalent radical including at least two carbon atoms directly linked to each other and included within the polyacetal polymer chain between the two valances.

8. The article of claim 7 wherein —OR— is oxyethylene.

9. In a process for producing a sterilant package including an article to be sterilized, the improvement comprising:

including in the interior of the sterilant package a polyacetal containing oxymethylene groups and stabilizing groups linked to the oxymethylene groups to prevent chain cleavage, said polyacetal having been subjected to high energy irradiation, prior to subjecting said package to heat sterilization, in a dose of from 0.01 to 400 megarads sufficient to effect chain cleavage without depolymerization to increase formaldehyde release upon subsequent heating of the package.

10. The process of claim 9 wherein the polyacetal is included as a separate piece in the package.

11. The process of claim 9 wherein said polyacetal is included by forming an interior portion of the package from said polyacetal.

12. The process of claim 9 wherein the stabilizing group is —OR— wherein R is a divalent radical including at least two carbon atoms directly linked to each other and included with the polyacetal polymer chain between the two valences.

13. The process of claim 12 wherein —OR— is oxyethylene.

* * * * *